United States Patent [19]
Mühlhoff

[11] Patent No.: US 6,337,920 B1
[45] Date of Patent: Jan. 8, 2002

(54) LASER SCANNING OPHTHALMOSCOPE

(75) Inventor: Dirk Mühlhoff, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/715,197

(22) Filed: Nov. 20, 2000

Related U.S. Application Data

(63) Continuation of application No. 09/129,131, filed on Aug. 4, 1998, now abandoned.

(30) Foreign Application Priority Data

Aug. 6, 1997 (DE) .......................................... 197 33 995

(51) Int. Cl.[7] ................................................. G06K 9/00
(52) U.S. Cl. ............................ 382/128; 351/200; 606/4
(58) Field of Search ................................ 382/100, 128, 382/117, 318, 324; 351/200, 205, 206; 359/368; 424/427; 600/318; 606/4

(56) References Cited

U.S. PATENT DOCUMENTS

| | | | |
|---|---|---|---|
| 4,213,678 A | 7/1980 | Pomerantzeff et al. .......... 351/7 |
| 4,579,430 A | 4/1986 | Bille .......................... 351/206 |
| 4,580,559 A | * 4/1986 | L'Esperance ............... 128/303 |
| 4,768,873 A | 9/1988 | Webb ......................... 321/205 |
| 5,066,116 A | 11/1991 | Sekine ....................... 351/221 |
| 5,071,246 A | * 12/1991 | Blaha et al. ................ 351/221 |
| 5,252,559 A | * 10/1993 | Sukigara et al. ............ 351/221 |
| 5,268,711 A | * 12/1993 | Poxleitner et al. .......... 351/214 |
| 5,396,302 A | 3/1995 | Triller et al. |
| 5,430,509 A | 7/1995 | Kobayashi ................... 351/221 |
| 5,784,148 A | 7/1998 | Heacock ...................... 351/221 |
| 5,892,569 A | * 4/1999 | Van de Velde .............. 351/221 |
| 6,099,127 A | * 8/2000 | Manivannan et al. ........ 351/221 |

FOREIGN PATENT DOCUMENTS

| EP | 0279589 | 8/1988 |
| EP | 0495469 | 7/1992 |
| EP | 0615721 | 9/1994 |

* cited by examiner

Primary Examiner—Jayanti K. Patel
(74) Attorney, Agent, or Firm—Walter Ottesen

(57) ABSTRACT

The invention is directed to a laser scanning ophthalmoscope for viewing the ocular fundus of the eye of a patient. A laser source generates a laser beam and a first scanner imparts an oscillatory deflection to the laser beam in a first direction. A second scanner imparts an oscillatory deflection to the laser beam in a second direction and transmits the oscillating laser beam toward the ocular fundus. At least a portion of the light of the laser beam is reflected from the ocular fundus and a detector detects the reflected light. A display displays an image defined by the light reflected from the ocular fundus and a control is connected to the display for selecting a sectional image of the image and the sectional image corresponds to a subregion of the ocular fundus. A drive motor pivotally moves at least one of the first and second scanners and a drive unit controls the drive motor. An interface connects the control to the drive unit.

15 Claims, 4 Drawing Sheets

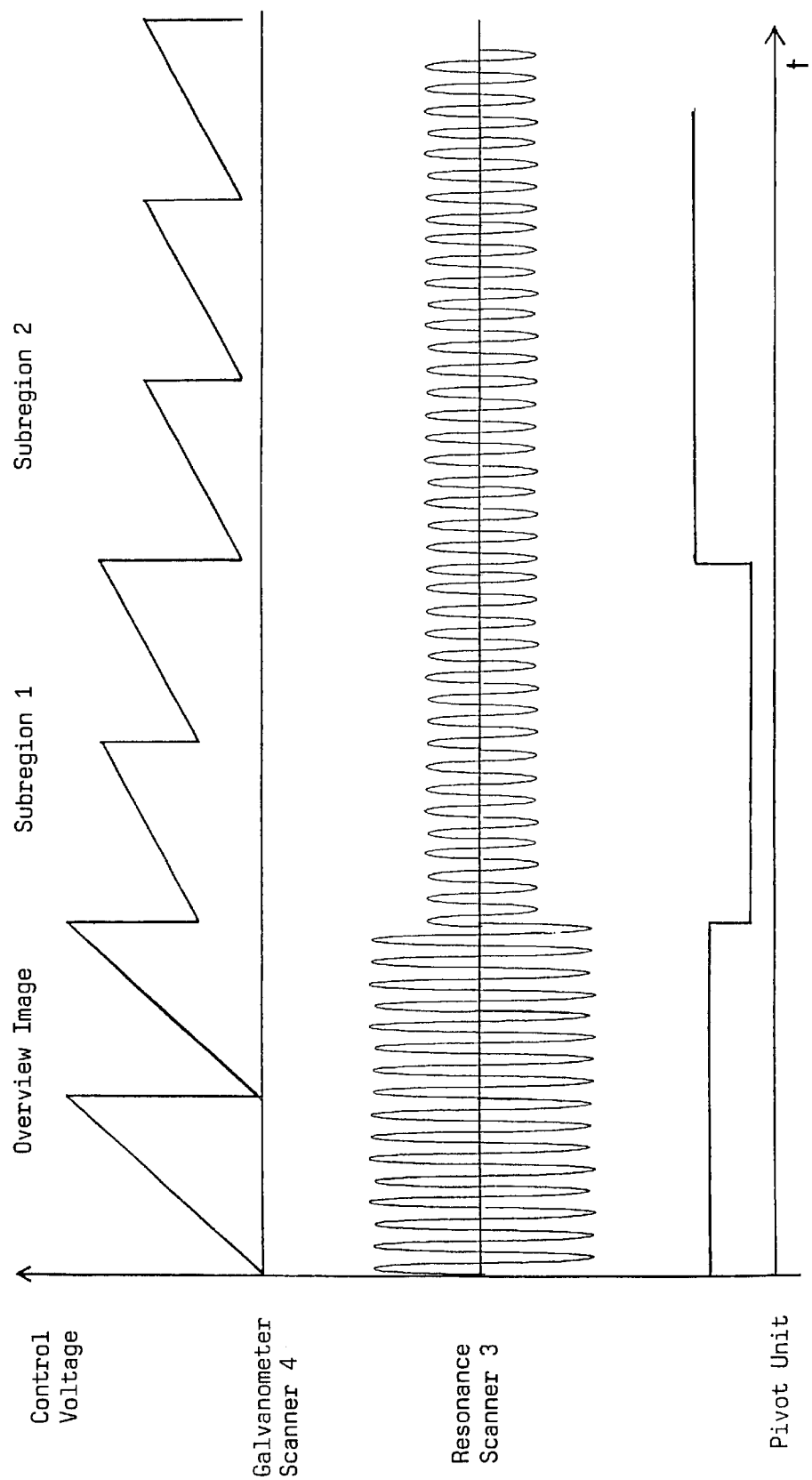

LASER SCANNING OPHTHALMOSCOPE

This is a continuation of application Ser. No. 09/129,131, filed Aug. 4, 1998 now abandoned.

FIELD OF THE INVENTION

The invention relates to an arrangement for raster scanning the ocular fundus utilizing a laser light source.

BACKGROUND OF THE INVENTION

Arrangements of the kind referred to above are known as scanning laser ophthalmoscopes (SLO or LSO). Scanning ophthalmoscopes are utilized for performing fluorescence angiography.

The largest possible viewing field is observed during the inflow phase of the fluorescence material. In the late phase, interesting areas, such as the capillary system, are observed with higher spatial resolution. For this purpose, it is known to change the imaging scale of the apparatus used. The number of image points per image is usually constant. From this, it becomes necessary to reduce the image field to increase the spatial resolution.

The following solutions are known:

(1) To increase the resolution, the apparatus includes, for example, a changeable optical element, such as a movable mirror as disclosed in European patent publication 0,495,469. The actuation of this optical element leads to the condition that the scanned field changes its size. The aspect ratio of the field does not change and both fields have the same center point. A simultaneous shift of the center point is not possible. The shift of the center point is necessary in order to obtain a high resolution image in the peripheral region and is done manually by the operator. For this purpose, the entire scanning system must be pivoted about the pupil of the patient.

(2) The apparatus scans over the entire region unchanged but only when the laser beam is disposed in the selected area is the detected signal utilized to build up the image (it is possible that also the laser is switched off during scanning of the area which is not selected in order to minimize the burden to the patient). This requires the digitalization rate to be changeable. The disadvantage here is that the recording time per pixel reduces when the image section is smaller and therefore the number of photons received per pixel. This leads to a reduction of the signal/noise ratio and therefore to a reduction of the image quality.

In U.S. Pat. No. 5,396,302, the imaging scale (and therefore the scan angle in the horizontal direction) is changed via two exchangeable mirrors. A scan angle change in the vertical direction is controlled via the control of a galvanometer scanner.

In European patent publication 0,279,589, eye movements are compensated by tracking utilizing two galvanometer scanners.

In European patent publication 0,615,721, acoustic-optical deflectors as horizontal scanners as well as resonance scanners are described in an arrangement of three or more scanners. Resonance scanners afford the advantage compared to galvanometer scanners that they have a higher frequency of oscillation and comprise a pivot mirror on a torsion rod in a housing. The mirror is electrically driven to oscillate at the natural frequency about its center point. Resonance scanners afford the advantage relative to polygon scanners that the scan angle is changeable via the electrical drive control.

SUMMARY OF THE INVENTION

It is an object of the invention to make different areas of the ocular fundus accessible to the viewer during the scanning operation without deteriorating the image quality.

The laser scanning ophthalmoscope of the invention is for viewing the ocular fundus of the eye of a patient. The laser scanning ophthalmoscope includes: a laser source generating a laser beam; a first scanner for imparting an oscillatory deflection to the laser beam in a first direction; a second scanner for imparting an oscillatory deflection to the laser beam in a second direction and for transmitting the oscillating laser beam toward the ocular fundus whereby at least a portion of the light of the laser beam is reflected from the ocular fundus; detector means for detecting the light reflected from the ocular fundus; a display for displaying an image defined by the light reflected from the ocular fundus; control means connected to the display for selecting a sectional image of the image and the sectional image corresponding to a subregion of the ocular fundus; a drive motor for pivotally moving at least one of the first and second scanners; a drive unit for controlling the drive motor; and, an interface for connecting the control means to the drive unit.

The invention makes it possible, during the scanning operation, to scan a smaller area or subregion of the entire scannable region at a high line frequency. This subregion can be at any desired location in the entire scannable region and the scanning of the subregion takes place with the same pixel frequency and with the same image buildup time as scanning the entire scannable region.

Accordingly,it is made advantageously possible to change the subregion to be scanned in size and position during the investigation with a scanning ophthalmoscope.

The center point of the new subregion to be scanned must not be in the center point of the previous subregion to be scanned. It is therefore no longer necessary for the operator to move the apparatus. Furthermore, the subregion of interest remains continuously under observation during the zooming operation.

Furthermore, the invention permits the subregion to be scanned to wander over the entire region to be scanned without it being necessary for the operator to move the apparatus.

The laser scan ophthalmoscope according to the invention continuously defines an image of the ocular fundus on a PC monitor. If a subregion of the image is of special interest, then this subregion can be selected by key or lever combinations or by pulling a window with the mouse of the PC. A control unit (PC) detects the coordinates of this subregion and emits control signals to the drive or control of the horizontal and vertical scanners as well as to a pivot unit. The scanners thereupon change their amplitudes and their oscillating zero points so that only the previously selected subregion is scanned. A galvanometer scanner is usually utilized as a slow vertical scanner. For such a scanner, the amplitude of the scan and the center of the scan can be varied without additional complexity by varying the amplitude or the offset of the control voltage.

Rapid mechanical horizontal scanners do not operate pursuant to this principle and therefore do not afford the possibility of changing the subregion to be scanned while maintaining a constant pixel frequency. This problem is solved by the electronic/mechanical solution according to the invention.

Several advantageous embodiments are provided for changing the subregion to be scanned at least in the direction of the rapid horizontal scan.

The scanning ophthalmoscope includes a motorized control which can pivot the entire scanning system (both scanners including housing) about the pupil of the patient. The motorized pivot arrangement is controlled by a PC.

The resonance scanner is securely held in a rotational bearing. In this rotational bearing, the resonance scanner can be rotated by a motor about its oscillatory axis. A rotation about this axis shifts the zero point of oscillation of the scanner and therefore shifts the center of the subregion to be scanned in the horizontal direction.

As will be explained below, this motorized control is driven by a control unit.

The scan system includes an adjustable mirror or scanner whose shift or scan direction is parallel to the direction of the rapid horizontal scanner. This mirror or scanner is preferably disposed between the rapid horizontal scanner and the slow vertical scanner. The center of the scan shifts in the direction of the rapid horizontal deflection because of a rotation of this additional mirror or scanner.

In view of the above, it is possible to do the following according to the invention:

(a) select and scan a desired subregion of the total region to be scanned;

(b) move the subregion to be scanned over the entire scannable region via a key control or by the operator;

(c) move the subregion to be scanned on a predetermined path over the entire scannable region and record images during this movement; and, (d) place the images one next to the other via image processing in order to obtain a high-resolution total image.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
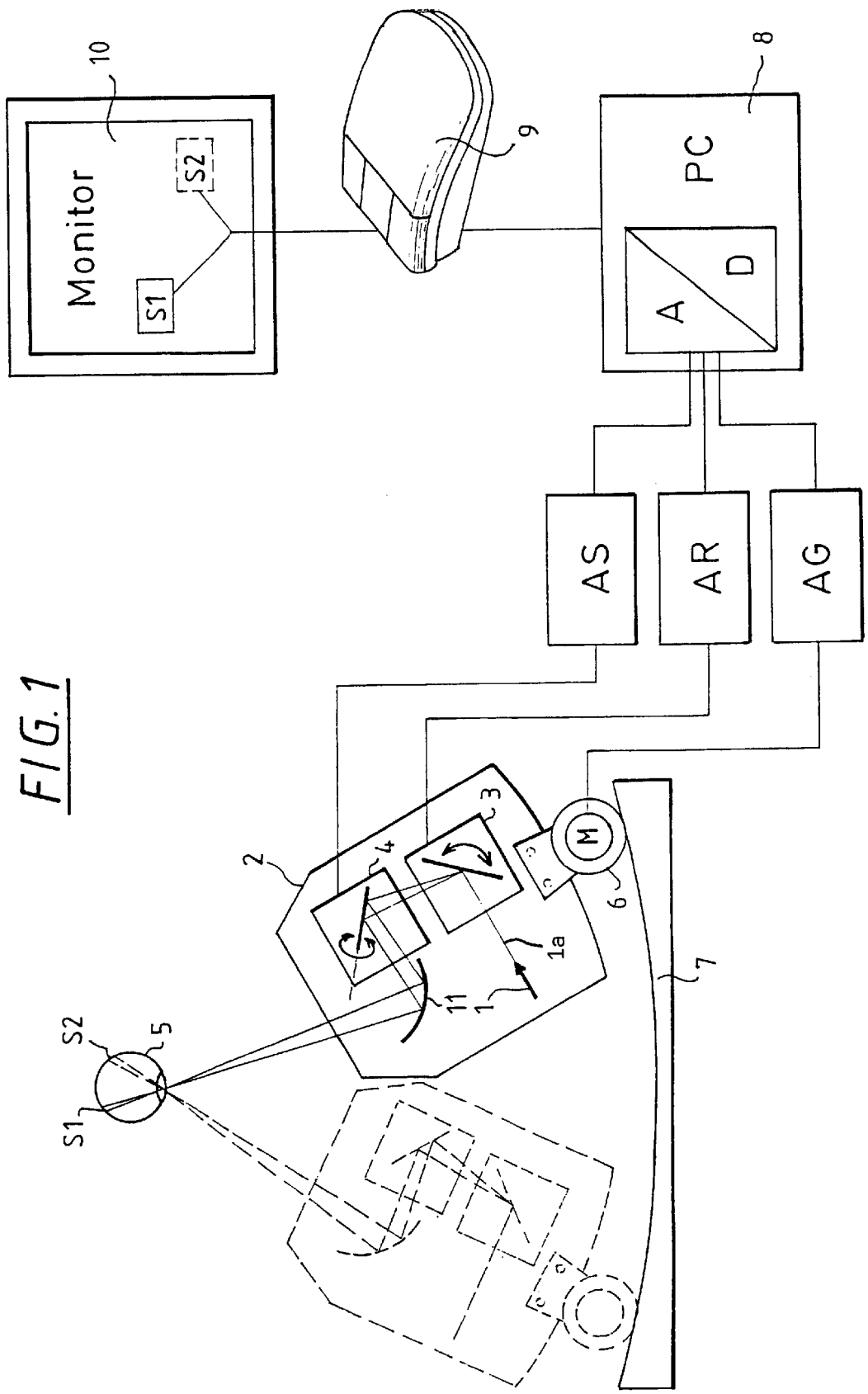
FIG. 1 is a schematic showing the motor-driven pivoting action of an embodiment of the entire laser scanning ophthalmoscope according to the invention.

In FIG. 1, reference numeral 1 identifies a schematic representation of a laser generating a laser beam 1a. The laser 1 is integrated in a housing 2 as shown or is supplied via a light conductor. The laser beam 1a reaches the eye and the ocular fundus via a resonance scanner 3, a galvanometer scanner 4 as well as an imaging mirror 11. The resonance scanner 3 provides rapid horizontal deflection and the galvanometer scanner 4 provides a slower vertical deflection. The imaging mirror 11 can be realized also as a lens optic. The galvanometer scanner 4 can, as will be explained below, shift its oscillating center point vertically at an angle. This corresponds to a vertical shift on a monitor 10 from image S1 to image S2. Images S1 and S2 correspond to two scanned subregions on the ocular fundus. The horizontal shift is generated in that the housing 2, with its entire scanning arrangement, undergoes an arcuately-shaped movement on an arcuately-shaped guide via a motor 6. The center of rotation of the guide is preferably coincident with the pupil of the eye 5 and the motor 6, which is connected to the housing 2, operatively engages the guide 7, for example, via toothed gears.

In lieu of an arcuate-shaped guide, the housing 2 can be journalled on an axis having an imaginary extension on which the pupil of the eye lies. The motor 6, resonance scanner 3 and galvanometer scanner 4 are connected to the drive units AS, AR and AG, respectively, which, in turn, are connected to a PC 8 which has a manually-actuated control 9 in the form of a mouse.

A total image of the ocular fundus is formed, for example, for a center position of the housing 2 between the positions S1 and S2 and by operating the resonance scanner 3 and the galvanometer scanner 4 at full amplitude. The viewer can select a sectional image such as (S1, S2) on the monitor by means of the mouse 8 and thereby trigger a drive of the motor 6 for controlling the horizontal position and for fixing the amplitude of the resonance scanner 3 in correspondence to the selected horizontal size of the image subregion. At the same time, the vertical center position of the galvanometer scanner 4 as well as its amplitude are adjusted.

For preadjusted scanners (3, 4), the horizontal position can also be adjusted via a handle (not shown) on the housing 2 when the apparatus is switched over to manual operation.

Figure 2:
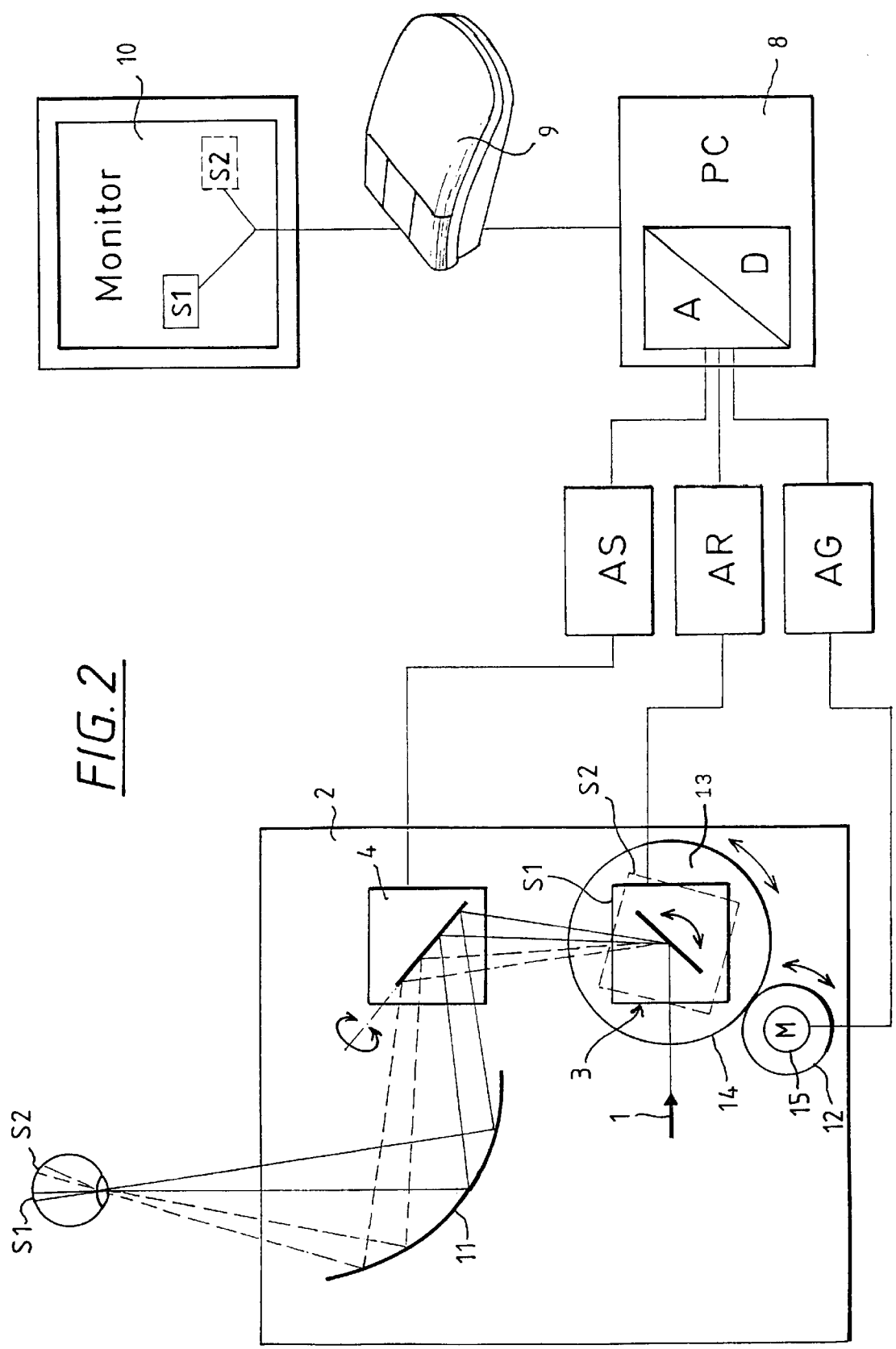
FIG. 2 is a schematic showing an embodiment of the invention equipped with a pivotable horizontal scanner.

A further advantageous embodiment of the invention is shown in FIG. 2. In this embodiment, the resonance scanner 3 including a pivot mirror 3a and torsion rod (not shown) thereof are integrated into a horizontally pivotable holder 13 and the pivot movement of the holder 13 is realized by means of a pivot motor 15 which engages in the holder 13 of the resonance scanner. This engagement takes place, for example, via gear wheel transmission (12, 14). The resonance scanner 3 changes its position as an entirety. For this purpose, flexible supply lines (not shown) from the drive unit AR to the resonance scanner 3 can be provided.

The functions described with respect to FIG. 1 can be realized in the same manner in the arrangement of FIG. 2.

Figure 3:
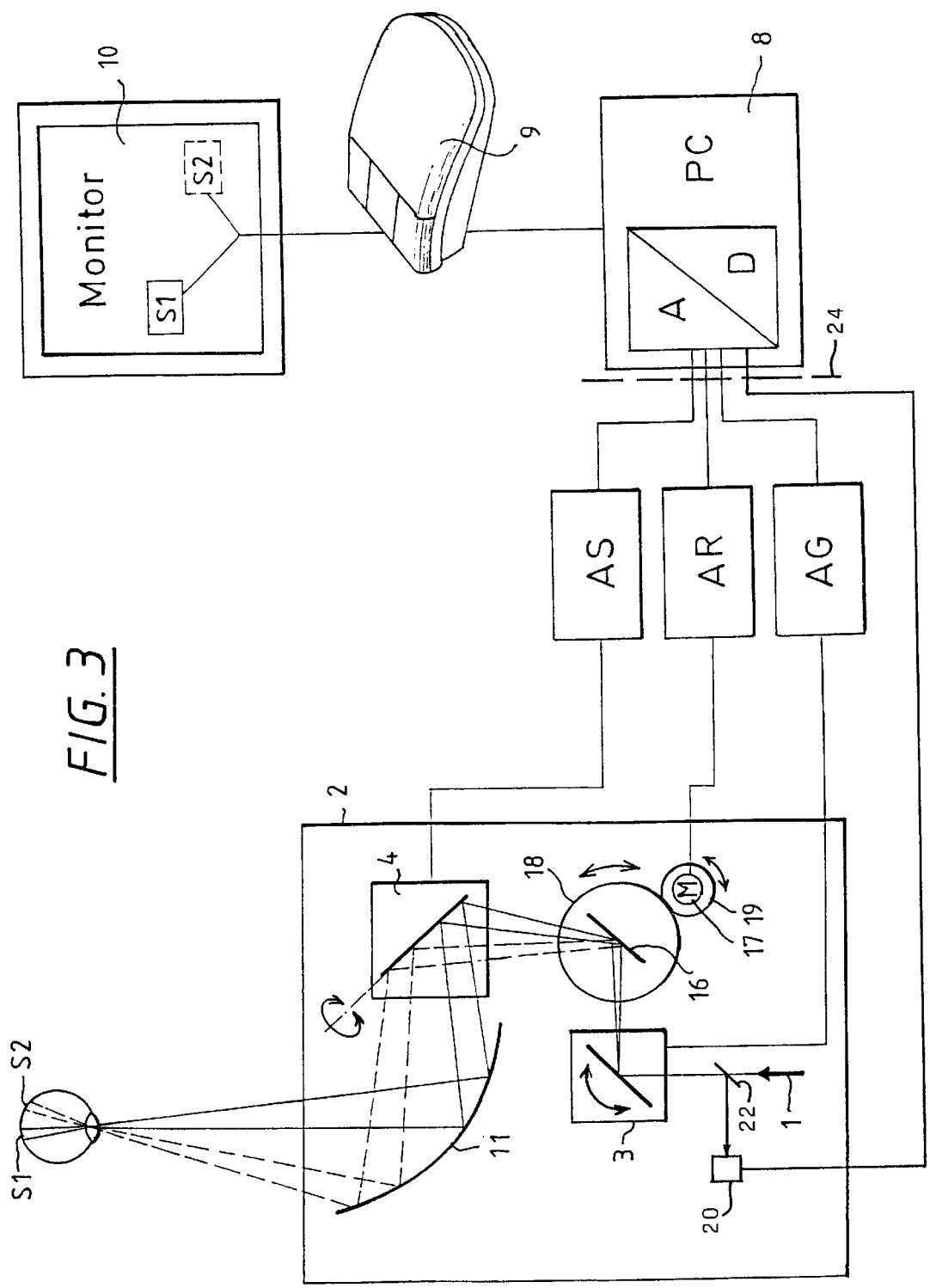
FIG. 3 is a schematic of an additional mirror disposed between the horizontal and vertical scanners; and, FIG. 4 is a schematic of the waveforms of the respective drive signals of the vertical scanner, horizontal scanner and an additional pivot unit.

Referring now to FIG. 3, in addition to the elements already described, the arrangement of FIG. 3 includes an additional scan mirror 16 which is arranged between resonance scanner 3 and galvanometer scanner 4. The scan mirror 16 can be horizontally driven via a motor 17 and can be pivoted by gear wheel transmission (18, 19).

The mirror 16 is moved in the horizontal direction in dependence upon a change of the selected subregion on the monitor 10 in accordance with the determination of the operator by means of the mouse 9. The mirror 16 has preferably a center position for generating a total image and, when adjusting a specific subregion, a horizontal pivoting takes place in the one or the other direction as indicated by the double arrow. This is shown with the positions and section images S1 and S2.

The pivot motor 17 is here suitable for slower movements; whereas, in contrast, for more rapid movements, the scan mirror 16 can be replaced by an additional galvanometer scanner whose scan direction runs parallel to that of the resonance scanner 3. In this way, the subregion can be moved more rapidly from one position to another on the monitor.

A detector 20 is provided to detect the light reflected from the eye. A beamsplitter 22 reflects this returning light out of the beam path and into the detector 20. The detector 20 emits an output signal representative of the reflected light and this signal is supplied to the PC 8. The laser scanning ophthalmoscope has an interface 24 to the PC 8 and the monitor 10.

In this arrangement and also in the arrangements of FIGS. 1 and 2, it is furthermore possible to automatically drive to several sectional images (preselected automatically or by the operator when they show image details of interest to the latter) sequentially via the described adjustments and to store the image or to superpose the selected sectional images on the previously recorded total image on the monitor 10.

FIG. 4 shows the schematic sequence of the control voltages which are generated by the drive units AS, AR and AG in order to carry out the functions of FIGS. 1 to 3 in accordance with the invention. In the transition from the total image of the ocular fundus with high amplitude of the galvanometer scanner 4 and the resonance scanner 3 to the subregion corresponding to sectional image S1 on the monitor 10, the amplitude of the control voltage for the scanners 3 and 4 is reduced and, simultaneously, an offset is added to the drive signal of the galvanometer scanner 4. The respective amplitudes still move from the minimum to the maximum value of the subregion and the offset then fixes the vertical position of this subregion.

In the resonance scanner 3, the amplitude has been reduced in correspondence to the horizontal expansion of the subregion. The horizontal position is changed in addition to the amplitude reduction by the displacement or pivoting in accordance with FIGS. 1 to 3. The voltage which operates on the pivot unit is proportional to the position thereof so that the pivot angle changes correspondingly in different directions from a center position via voltage reduction or voltage increase as shown.

For a reduction of the amplitude of the resonance scanner 3, the scan points, whose time-dependent spacing is pregiven by the frequency of the scanner, can advantageously lie closer next to each other so that the image resolution is increased.

This also applies to the drive of the galvanometer scanner 4 when its amplitude is reduced.

Furthermore, monitoring can take place by means of an eye-tracking unit as to whether the patient's eye has moved and a readjustment of the set investigative image can be made with respect to the patient movement via the drive units AS, AG and AR. Such a tracking unit is disclosed, for example, in European patent publication 0,615,721.

It is understood that the foregoing description is that of the preferred embodiments of the invention and that various changes and modifications may be made thereto without departing from the spirit and scope of the invention as defined in the appended claims.

What is claimed is:

1. A laser scanning ophthalmoscope for viewing the ocular fundus of the eye of a patient, the laser scanning ophthalmoscope comprising:
   a laser source generating a laser beam;
   a first scanner for imparting an oscillatory deflection to said laser beam in a first direction;
   a second scanner for imparting an oscillatory deflection to said laser beam in a second direction and for transmitting the oscillating laser beam toward said ocular fundus whereby at least a portion of the light of said laser beam is reflected from said ocular fundus;
   detector means for detecting the light reflected from said ocular fundus;
   a display for displaying an image defined by the light reflected from said ocular fundus;
   control means connected to said display for selecting a sectional image of said image and said sectional image corresponding to a subregion of said ocular fundus;
   a drive motor for pivotally moving at least one of said first and second scanners;
   a drive unit for controlling said drive motor; and,
   an interface for connecting said control means to said drive unit.

2. The laser scanning ophthalmoscope of claim 1, wherein said control means is a PC having a mouse.

3. The laser scanning ophthalmoscope of claim 1, wherein the control of the pivotal movement imparted to said one scanner is effected via said drive unit by selecting said subregion.

4. The laser scanning ophthalmoscope of claim 1, wherein said one scanner is pivoted via said drive motor driven by said drive unit.

5. The laser scanning ophthalmoscope of claim 1, wherein pivot movement is about a vertical axis.

6. A laser scanning ophthalmoscope for viewing the ocular fundus of the eye of a patient, the laser scanning ophthalmoscope comprising:
   a laser source generating a laser beam;
   a first scanner for imparting a deflection to said laser beam in a first direction;
   a second scanner for imparting a deflection to said laser beam in a second direction and for transmitting the oscillating laser beam toward said ocular fundus whereby at least a portion of the light of said laser beam is reflected from said ocular fundus;
   detector means for detecting the light reflected from said ocular fundus;
   a display for displaying an image defined by the light reflected from said ocular fundus;
   control means connected to said display for selecting a sectional image of said image and said sectional image corresponding to a subregion of said ocular fundus;
   an element for changing the direction of said laser beam;
   said element being disposed between said first and second scanners;
   a drive motor for pivotally moving said element so as to cause the pivot direction of said element to correspond to the scanning direction of said first scanner or said second scanner;
   a drive unit for controlling said drive motor; and,
   an interface for connecting said control means to said drive unit.

7. The laser scanning ophthalmoscope of claim 6, wherein said control means is a PC having a mouse.

8. The laser scanning ophthalmoscope of claim 6, wherein one of said first and second scanners is faster than the other one of said first and second scanners; and, the pivot direction of said element being coincident with the scanning direction of said one scanner.

9. The laser scanning ophthalmoscope of claim 6, wherein the control of the pivotal movement imparted to said element is effected via said drive unit by selecting said subregion.

10. The laser scanning ophthalmoscope of claim 8, wherein said one scanner is a resonance scanner oscillating about a vertical rotational axis.

11. The laser scanning ophthalmoscope of claim 10, wherein said other one of said first and second scanners is a galvanometer scanner.

12. In a laser scanning ophthalmoscope for viewing the ocular fundus of the eye of a patient, the laser scanning ophthalmoscope including: a laser source generating a laser beam; a first scanner for imparting an oscillatory deflection to said laser beam in a first direction; a second scanner for imparting an oscillatory deflection to said laser beam in a second direction and for transmitting the oscillating laser beam toward said ocular fundus whereby at least a portion of the light of said laser beam is reflected from said ocular fundus; detector means for detecting the light reflected from said ocular fundus; a display for displaying an image defined by the light reflected from said ocular fundus; control means connected to said display for selecting a sectional image of said image and said sectional image corresponding to a subregion of said ocular fundus; a drive motor for pivotally moving at least one of said first and second scanners; a drive unit for controlling said drive motor; and, an interface for connecting said control means to said drive unit; a method of operating said laser scanning ophthalmoscope comprising the steps of:

after selecting said subregion, detecting the coordinate of said subregion on said display;

pivoting at least one of said scanners in the direction of said subregion; and, adjusting the oscillatory amplitude for at least one of said first and second scanners.

13. The method of claim 12, wherein said first scanner is a resonance scanner oscillating about a vertical axis and said second scanner is a galvanometer scanner oscillating about a horizontal axis; and, wherein the method comprises the further steps of:

adjusting the amplitude of the oscillations of said scanners; and, superposing a signal onto said galvanometer scanner for changing the position of the center point of the oscillation thereof.

14. The method of claim 12, wherein said drive motor and said first and second scanners are driven in correspondence to pregiven positions of subregions; said subregions are driven to sequentially and are displayed sequentially or simultaneously on said display.

15. The method of claim 14, wherein a total image of the ocular fundus is detected and generated utilizing said scanners and said detector; and, superposing said subregions on said total image.

* * * * *